United States Patent [19]

Janisch et al.

[11] Patent Number: 5,455,368
[45] Date of Patent: Oct. 3, 1995

[54] PROCESS FOR SEPARATING OFF METHANOL FROM A MIXTURE OF DIMETHYL CARBONATE AND METHANOL

[75] Inventors: Ingo Janisch, Kürten; Heinz Landscheidt, Duisburg; Werner Strüver, Leverkusen; Alexander Klausener, Köln, all of Germany

[73] Assignee: Bayer Aktiengesellschaft, Leverkusen, Germany

[21] Appl. No.: 351,860

[22] Filed: Dec. 8, 1994

[30] Foreign Application Priority Data

Dec. 15, 1993 [DE] Germany ............ 43 42 713.8

[51] Int. Cl.⁶ ............ C07C 27/26; C07C 29/76; C07C 31/04; C07C 69/96
[52] U.S. Cl. ............ 558/277; 568/917
[58] Field of Search ............ 568/917; 558/277

[56] References Cited

U.S. PATENT DOCUMENTS

| | | |
|---|---|---|
| 4,162,200 | 7/1979 | Himmele et al. |
| 4,359,592 | 11/1982 | Chao et al. ............ 568/917 |
| 4,582,645 | 4/1986 | Spencer . |
| 5,142,087 | 8/1992 | Joerg et al. |
| 5,360,923 | 11/1994 | Nickel et al. ............ 558/277 |

FOREIGN PATENT DOCUMENTS

| | | |
|---|---|---|
| 0413215 | 2/1991 | European Pat. Off. . |
| 0423949 | 4/1991 | European Pat. Off. . |
| 2706684 | 7/1978 | Germany . |
| 2737265 | 3/1979 | Germany . |

OTHER PUBLICATIONS

Derwent Abstracts, Week 9040, 1 page; DAIL E17 90–301274/40 JO 2212–456–A; "Di:methyl carbonate sepn. by distn. of . . . " Daicel Chem. Ind, Feb. 13, 1989.

Chemical Abstracts, vol. 113, 1990, 1 page; CA#214642m: "Membrane process for separation of organic liquids", M. Pasternak et al.

Bayer's Patent Application (Le A 18 296); DE 2,737,265; "Process for separating off dimethyl carbonate", 3 pages. (1979).

*Primary Examiner*—Joseph E. Evans
*Attorney, Agent, or Firm*—William C. Gerstenzang; Sprung Horn Kramer & Woods

[57] ABSTRACT

Methanol can be substantially removed from dimethyl carbonate (DMC)/methanol mixtures by absorption on ion exchange resins. The enriched DMC is obtained as filtrate. The absorption is carried out at from −50° C. to +100° C. and 0.1–10 bar.

10 Claims, No Drawings

PROCESS FOR SEPARATING OFF METHANOL FROM A MIXTURE OF DIMETHYL CARBONATE AND METHANOL

BACKGROUND OF THE INVENTION

In the industrial preparation of dimethyl carbonate (DMC), there is frequently formation of mixtures of DMC and methanol which may contain further constituents. Thus, for example, EP 413215 describes a process for preparing DMC in which DMC is formed in admixture with methanol and water.

However, to use DMC as reagent for further reactions, such as the transesterification of other carbonates, in particular to give diphenyl carbonate or other diaryl carbonates, but also aryl alkyl, dialkyl and dialkenyl carbonates, it is necessary to be able to use it in essentially pure form, in particular essentially free of methanol. For this purpose, an effective process for very complete separation of other materials, in particular of methanol, from mixtures of DMC with such other materials is of great importance.

In numerous uses of DMC, for example for carrying out transesterification reactions, in particular for the preparation of monoaryl and diaryl carbonates, it is not possible to make the DMC react completely. Such reactions give, besides the desired reaction products, mixtures which, in addition to the methanol liberated, sometimes also contain appreciable amounts of the unreacted useful material DMC.

Separation of methanol from such mixtures in very pure form allows, on the one hand, its renewed provision for an economic use, e.g. for the purpose of recycling to the preparation process for DMC. On the other hand, the residual amounts of DMC present in such mixtures are recovered in usably enriched form, which is a further economic advantage.

It can therefore be said in summary that, in particular for the purpose of possible use of DMC as substitute material for the highly toxic phosgene, there has to be available not only an economically satisfactory preparation process, but also an efficiently operating separation process for the abovementioned mixtures of methanol and DMC and possibly further components.

The mixture specified can be separated by distillation only with great difficulty, i.e. not in a simple manner, since DMC forms an azeotrope with methanol at atmospheric pressure, this azeotrope having the approximate composition 70% of methanol, 30% of DMC.

Separation of such mixtures by exploitation of the pressure dependence of the composition of the azeotrope, for instance by distillation at higher or lower pressures than atmospheric pressure or by successive distillation at higher and lower pressures than atmospheric pressure (two-pressure distillation), as is described, for example, in JP 02212456 (cited according to CA 114, 81029), is associated with high energy and capital costs.

To carry out a distillative separation of mixtures of methanol and DMC, it has also been proposed that the distillation be carried out with the addition of further auxiliaries. Thus, according to German Offenlegungsschrift 2737265, the addition of hydrocarbons such as n-heptane is supposed to make possible a separation of the two components by means of azeotropic distillation; according to German Offenlegungsschrift 2706684, the distillative separation of mixtures of DMC and methanol can be carried out by means of an extractive distillation with the addition of organic solvents such as methyl-glycol acetate. In both variants, it is necessary to separate off the auxiliary and circulate it. In addition, the purity of the dimethyl carbonate can be impaired by the presence of further materials.

Besides these thermal processes, other processes for separating off methanol from mixtures with DMC have also been proposed. Thus, for example, U.S. Pat. No. 4,960,519 describes pervaporation on specific membranes. However, this separation technique generally has to be carried out in association with additional distillative separation operations and, owing to the complicated apparatus used, is associated with high costs which make industrial utilization seem questionable.

Furthermore, U.S. Pat. No. 4,582,645 proposes removing DMC from mixtures by absorption on zeolites. Owing to the limited absorption capacity of the zeolites (100 mg of DMC/2.5 g of zeolite), only small amounts of DMC can be separated off in this way. This process is therefore only suitable for mixtures whose DMC content is small.

It is accordingly an object of the invention to find a process which makes it possible to separate off methanol from mixtures with DMC in an economically useful manner.

SUMMARY OF THE INVENTION

It has surprisingly been found that treatment of mixtures containing DMC and methanol with ion exchange resins selectively removes methanol from these mixtures, so that substantially methanol-free DMC of high purity is obtained. The methanol content is 0.01–40% by weight, based on the weight of the mixture.

The process of the invention is, in principle, also suitable for those mixtures containing methanol and dimethyl carbonate which may also contain further materials. Preference is given to using mixtures whose methanol content is a maximum of 30% by weight, particularly preferably those whose methanol content is a maximum of 10% by weight.

The invention provides a process for separating off methanol from a mixture of dimethyl carbonate (DMC) and methanol, in which the methanol content is 0.01–40% by weight, based on the weight of the mixture, which is characterized in that such a mixture is treated at from −50° C. to +100° C. and 0.1–10 bar with an ion exchanger in an amount of 1–100% of the weight of the mixture.

DETAILED DESCRIPTION OF THE INVENTION

In one embodiment of the process, the DMC/methanol mixture, which can possibly contain further materials, is admixed with ion exchange resin. After a time sufficient for absorption of the methanol by the ion exchange resin in question, which time can be determined, for example, by gas chromatographic analysis of the supernatant liquid at certain time intervals, the resin is mechanically separated off by filtration. The amount of the ion exchange resin used is here generally 1–100%, preferably 5–50%, of the weight of the mixture to be freed of methanol.

Further materials, which may be present, are, for example, water, ethylene glycol, propylene glycol, ethylene or propylene glycol carbonate, dimethyl oxalate, methyl formate and formaldehyde dimethylacetal.

In another embodiment, a stream of the DMC/methanol mixture to be treated, which can possibly contain further constituents as can be formed, for example, in the preparation of DMC, is passed through a column which is packed with the ion exchange resin. The throughput over the ion exchanger is here 1–100 volume units of the mixture to be separated per volume unit of the ion exchange resin per hour, which essentially corresponds to the above weight ratio. This embodiment can be carried out using a pseudocontinuous procedure by using one column until it is exhausted and subsequently switching to a fresh column while the first column is regenerated.

The process of the invention can be carried out at temperatures of from −50° to 100° C., preferably at from −20° to 100° C., particularly preferably at 0°–50° C.

The process of the invention can be carried out in a pressure range of from 0.1 to 10 bar.

Suitable absorber resins for carrying out the process of the invention are, for example, synthetic ion exchangers containing Groups which exchange cations or anions, or mixtures of such ion exchangers.

Such ion exchangers have, for example, a matrix based on cross-linked styrene polymers. Cross-linkers which may be mentioned are, for example, divinylbenzene, trivinylbenzene or trivinylcyclohexane in an amount of 1–80% by weight, based on the total amount of the comonomers.

However, the matrix can, optionally, also be a phenol-formaldehyde condensate, an acrylic resin, a methacrylic resin or an epichlorohydrin-polyamine condensate, in each case in cross-linked form with the above cross-linkers. Such cross-linked matrices can be used in the Gel or the macroporous form.

Examples of functional Groups of the cation exchangers which may be mentioned are: sulphonic acid Groups, phosphonic acid Groups and carboxyl Groups, in each case in the H+ form or in the metal ion or cation form. Mention may be made of the following examples of metal ions or cations suitable for this purpose: Li+, Na+, K+, Rb+, Cs+, $NH_4^+$, $Cu^{2+}$, Ag+, $Mg^{2+}Ca^{2+}$ $Ba^{2+}$, $Zn^{2+}$, $Al^{3+}$, $Sn^{2+}$, $Pb^{2+}Ce^{4+}$ $UO_2^{2+}$, $Cr^{3+}Co^{2+}+$, $Ni^{2+}Fe^{2+}$, $Fe^{3+}$ or $Pd^{2+}$.

Functional groups of the anion exchangers can be, for example: nitrogen-containing functional groups of the type —$NR_3$ such as —$N(CH_3)_3$ +or —$(CH_3)_2CH_2CH_2OH$, furthermore nitrogen-containing functional groups of the type —$NR_2$, such as —$N(CH_3)_2$, and also N-oxide groups. Such nitrogen-containing functional groups can, for example, contain ions selected from the group consisting of OH−, Cl− and $SO_4^{2-}$ as exchangeable counter-ion. Apart from $CH_3$ and $CH_2CH_2OH$, R can be ethyl, propyl, isopropyl, butyl, isobutyl, benzyl or phenyl, of which various ones can also occur on an N atom.

Ion exchangers of the type described have for example total ion exchange capacities of about 0.2–6 equivalents/l. Such resins and their preparative processes have been known for a long time (Ullmanns Enzyklopä der technischen Chemie, 4th Edition/Volume 13, pp. 279 ff, Verlag Chemie, 1977).

Examples of resins which can be used according to the invention are: styrene-divinylbenzene gel resins containing sulphonic acid groups, macroporous styrene-divinylbenzene resins containing sulphonic acid groups, gel or macroporous acrylic acid-divinyl benzene resins containing carboxyl groups, gel or macroporous styrene-divinylbenzene resins containing —$N(CH_3)$ groups, weak-base, macroporous resins of the acrylamide-divinylbenzene type, strong-base, macroporous resins of the acrylamidedivinylbenzene type or cross-linked phenol-formaldehyde resins containing sulphonic acid groups.

This list is not complete and does not imply limitation to the resins specified.

Many of the specified resins are commercial products of various manufacturers.

Preference is given to using cation exchangers, particularly in a form loaded with metal cations. The methanol-containing ion exchange resins formed in the course of the process of the invention can be easily regenerated by heating in vacuo or in a stream of gas.

The methanol which is again liberated can either be trapped by cooling, or the methanol-containing gas streams obtained can be used for chemical reactions, preferably for the preparation of DMC.

EXAMPLES

Example 1

Styrene-divinylbenzene (DVB) gel polymer containing sulphonic acid groups (commercial product newatit®SC 104 from Bayer AG), which was moist with water, was dried for 24 hours at 80° C. and 250 mbar.

10 g of the exchanger resin pretreated in this way were added to a mixture of 95 g of dimethyl carbonate and 5 g of methanol. The mixture was stirred at room temperature. After 30 minutes it was filtered and the filtrate was analysed by gas chromatography.

The DMC content of the filtrate was then above 98%.

Examples 2 to 7

The resins shown in Table 1 were each pretreated as in Example 1. The further experimental procedure was likewise as described in Example 1. In each case, the starting concentrations of the dimethyl carbonate/methanol mixtures and the concentrations of the filtrate obtained after a contact time of 3 hours are given.

TABLE 1

| Example | Exchanger resin | Description | DMC concentration Feed | DMC concentration Filtrate |
|---|---|---|---|---|
| 2 | gel containing sulphonic acid groups | Bayer-Katalysator K 1131 ® | 95% | 97.9% |
| 3 | gel containing sulphonic acid groups | Bayer-Katalysator K 1131 ® | 90% | 94.1% |
| 4 | gel containing sulphonic acid groups | strong-acid ion exchanger containing 4% cross-linker (DVB) | 90% | 94.0% |
| 5 | gel containing sulphonic acid groups | strong-acid ion exchanger containing 3% of cross-linker (DBB) | 90% | 94.1% |
| 6 | macroporous containing trimethylammonium groups | Lewatit ® MP 500 | 90% | 92.5% |
| 7 | gel containing sulphonic acid groups | Bayer-Katalysator K 1131 ® loaded with K+ | 90% | 91.2% |

Example 8

A mixture of 95 g of dimethyl carbonate and 5 g of methanol was passed, over a period of 3 hours, through a column containing 10 g of styrene-divinylbenzene gel polymer containing sulphonic acid groups (commercial product K 1131®from Bayer AG).

The eluate collected was analysed by gas chromatography.

After 1 hour, the eluate had a composition of 99.8% of dimethyl carbonate and 0.2% of methanol.

After 3 hours, the eluate contained 99.7% of dimethyl carbonate.

What is claimed is:

1. A process for separating off methanol from a mixture of dimethyl carbonate (DMC) and methanol, in which the methanol contents is 0.01–40% by weight, based on the weight of the mixture, wherein such a mixture is treated at from −50° C. to +100° C. and 0.1–10 bar with an ion exchanger in an amount of 1–100% of the weight of the mixture.

2. The process of claim 1, wherein the mixture to be treated contains 0.01–30% by weight of methanol.

3. The process of claim 2, wherein the mixture to be treated contains 0.01–10% by weight of methanol.

4. The process of claim 1, wherein the ion exchanger is used in an amount of 5–50% of the weight of the mixture to be treated.

5. The process of claim 1, which is carried out at from −20° to +100° C.

6. The process of claim 5, which is carried out at 0°–50° C.

7. The process of claim 1,, wherein the ion exchanger used is a cation exchanger, an anion exchanger or a mixture of both 8. The process of claim 1, wherein the treatment with an ion exchanger is carried out in pseudocontinuous column operation 9. The process of claim 7, wherein a cation exchanger is used.

10. The process of claim 9, wherein a cation exchanger loaded with metal ions is used.

* * * * *